(12) United States Patent
Zubrod

(10) Patent No.: US 10,433,858 B2
(45) Date of Patent: Oct. 8, 2019

(54) METHOD FOR MANUFACTURING SURGICAL INSTRUMENT

(71) Applicant: RZ-Medizintechnik GmbH, Tuttlingen (DE)

(72) Inventor: Tobias Zubrod, Tuttlingen (DE)

(73) Assignee: RZ-Medizintechnik GmbH, Tuttlingen (DE)

( * ) Notice: Subject to any disclaimer, the term of this patent is extended or adjusted under 35 U.S.C. 154(b) by 336 days.

(21) Appl. No.: 15/401,517

(22) Filed: Jan. 9, 2017

(65) Prior Publication Data

US 2017/0196578 A1 Jul. 13, 2017

(30) Foreign Application Priority Data

Jan. 8, 2016 (DE) .................. 10 2016 200 131

(51) Int. Cl.

| | |
|---|---|
| *A61B 17/28* | (2006.01) |
| *A61B 17/02* | (2006.01) |
| *B33Y 80/00* | (2015.01) |
| *B33Y 10/00* | (2015.01) |
| *B33Y 50/00* | (2015.01) |
| *A61B 18/14* | (2006.01) |
| *B29C 64/00* | (2017.01) |
| *A61B 17/30* | (2006.01) |
| *A61B 17/00* | (2006.01) |
| *G06F 19/00* | (2018.01) |

(52) U.S. Cl.
CPC .............. *A61B 17/28* (2013.01); *A61B 17/02* (2013.01); *A61B 18/1442* (2013.01); *B29C 64/00* (2017.08); *B33Y 10/00* (2014.12); *B33Y 50/00* (2014.12); *B33Y 80/00* (2014.12); *A61B 17/30* (2013.01); *A61B 2017/00526* (2013.01); *A61B 2018/1462* (2013.01); *G06F 19/3481* (2013.01)

(58) Field of Classification Search
CPC ........ A61B 17/2841; A61B 17/28; B25B 7/00
See application file for complete search history.

(56) References Cited

U.S. PATENT DOCUMENTS

| | | | | |
|---|---|---|---|---|
| 6,772,026 | B2 * | 8/2004 | Bradbury | G16H 50/50 |
| | | | | 700/98 |
| 8,931,880 | B2 * | 1/2015 | Murphy | B41J 3/407 |
| | | | | 347/20 |
| 9,289,267 | B2 * | 3/2016 | Sauer | A61B 34/20 |
| 9,428,254 | B1 * | 8/2016 | Scheller | B63B 35/7953 |
| 10,155,273 | B1 * | 12/2018 | Jessen | G05B 15/02 |
| 2004/0243481 | A1 * | 12/2004 | Bradbury | G16H 50/50 |
| | | | | 705/26.1 |
| 2009/0254367 | A1 * | 10/2009 | Belcher | B33Y 80/00 |
| | | | | 705/2 |
| 2013/0203031 | A1 * | 8/2013 | Mckinnon | A61F 2/46 |
| | | | | 434/262 |
| 2013/0245801 | A1 * | 9/2013 | Schroeder | A61F 2/30 |
| | | | | 700/98 |

(Continued)

*Primary Examiner* — Cachet I Proctor
(74) *Attorney, Agent, or Firm* — Akerman LLP; Peter A. Chiabotti; Mammen (Roy) P. Zachariah, Jr.

(57) ABSTRACT

A method for manufacturing a surgical instrument, comprising the steps of selection of a value for at least one parameter of the surgical instrument in a configuration program, automated generation of configuration data from the selected values by the configuration program, transfer of the configuration data to a 3D printer, and printing of the surgical instrument by means of a 3D printer.

25 Claims, 12 Drawing Sheets

(56) References Cited

U.S. PATENT DOCUMENTS

| | | | | |
|---|---|---|---|---|
| 2014/0066977 | A1* | 3/2014 | Scheller | A61B 17/30 606/205 |
| 2014/0074272 | A1* | 3/2014 | Cowden, IV | G06F 17/50 700/97 |
| 2014/0277659 | A1* | 9/2014 | Kumar | G05B 19/4097 700/97 |
| 2014/0290707 | A1* | 10/2014 | O'Donnell | A45B 25/00 135/15.1 |
| 2015/0044420 | A1* | 2/2015 | Nowak | C09D 7/61 428/141 |
| 2015/0057702 | A1* | 2/2015 | Edmondson | A61B 17/28 606/207 |
| 2015/0081076 | A1* | 3/2015 | Fernandes | G06F 17/50 700/98 |
| 2015/0165690 | A1* | 6/2015 | Tow | B33Y 80/00 700/119 |
| 2015/0305762 | A1* | 10/2015 | Dunn | A61B 17/30 606/205 |
| 2015/0343708 | A1* | 12/2015 | Gerstle | B33Y 50/00 700/98 |
| 2016/0166330 | A1* | 6/2016 | Lawrence | A61B 17/3468 606/116 |
| 2016/0302800 | A1* | 10/2016 | Song | A61B 17/157 |
| 2016/0341517 | A1* | 11/2016 | Williams | F41C 23/10 |
| 2016/0349738 | A1* | 12/2016 | Sisk | B33Y 80/00 |
| 2016/0361844 | A1* | 12/2016 | Jackson | B29C 33/3835 |
| 2017/0072637 | A1* | 3/2017 | Yanazume | B33Y 50/02 |
| 2017/0265849 | A1* | 9/2017 | Assaf | A61B 17/12036 |
| 2017/0278301 | A1* | 9/2017 | Peterson | G06T 19/20 |
| 2018/0049738 | A1* | 2/2018 | Meloul | A61B 17/068 |
| 2018/0067340 | A1* | 3/2018 | Chumbley | G02C 5/12 |
| 2018/0169852 | A1* | 6/2018 | Fryer-Biggs | B26B 3/00 |

* cited by examiner

METHOD FOR MANUFACTURING SURGICAL INSTRUMENT

CROSS-REFERENCE TO RELATED APPLICATIONS

This application claims priority to German Patent Application No. 10 2016 200 131.0, filed Jan. 8, 2016, which is incorporated by reference in its entirety.

BACKGROUND

Many surgical instruments have a base body made of metal. Conventionally, it is milled or turned using tooling machines. In order to make the production of a specific surgical instrument with defined dimensions profitably, a larger number of the corresponding surgical instrument is generally manufactured in series and subsequently sold to various buyers over an extended period of time. In the event that instruments of a given type are to be offered with different dimensions, such a batch with a larger unit quantity must be manufactured for each of these types. In that case, the buyers are limited to the types of surgical instrument offered by the manufacturers. If custom-made products with customer-specific dimensions are to be produced, this is very cost-intensive and results in long lead times. In extreme cases, a surgical instrument with the optimal dimensions for a specific operation may not be available.

SUMMARY

The present disclosure provides a method for manufacturing a surgical instrument by means of which a large number of different surgical instruments can be made available in a simple manner.

The present application provides a method with the features and structures disclosed herein.

Advantageous embodiments and developments of the present disclosure are indicated in the features and structures disclosed herein.

The method according to the present application for manufacturing a surgical instrument has the following steps:

selection of a value for at least one parameter of the surgical instrument in a configuration program, automated generation of configuration data from the selected values by the configuration program, transfer of the configuration data to a 3D printer, and printing of the surgical instrument by means of a 3D printer.

With the aid of a 3D printer, three-dimensional elements can be constructed layer by layer. The construction is performed particularly in a computer-supported manner from one or more liquid or solid materials. Both plastics and metals, for example, merit consideration as material. Plastics can be supplied in solid form, for example as plastic wire, and fused before they are pressed through a nozzle and applied in the desired location. Metals can be provided in the form of a powder or granulate and melted and sintered at the desired location with the aid of a laser. To achieve this, the 3D printer requires the information with respect to the shape and dimensions of the element to be produced. This is made available to the 3D printer as configuration data. The present disclosure is based on the idea of providing a user of surgical instruments the opportunity to obtain a surgical instrument that is adapted specially to his own desires and requirements, ideally in order to have an optimally suitable instrument for each operation. Piece production of surgical instruments is inconceivable with conventional manufacturing methods, since they are disproportionately cost-intensive. Using the configuration program according to the present disclosure, however, a user is given the opportunity to advantageously select a desired value for at least one parameter of the surgical instrument. Based on the selected values, configuration data are generated in an automated manner by means of the configuration program and then provided to the 3D printer so that it can print the surgical instrument according to the user's needs. The fundamental idea of the configuration program is therefore that the user is able to optimally draw up the surgical instrument according to his wishes, upon which the desired surgical instrument can then be produced in make-to-order fashion by means of the 3D printer. Advantageously, the configuration program is provided to the user, for example on an internet page, while the 3D printer is located at the provider of the internet page, which, after an ordering process, manufactures the surgical instrument and ships the finished instrument.

DETAILED DESCRIPTION

Figure 1:
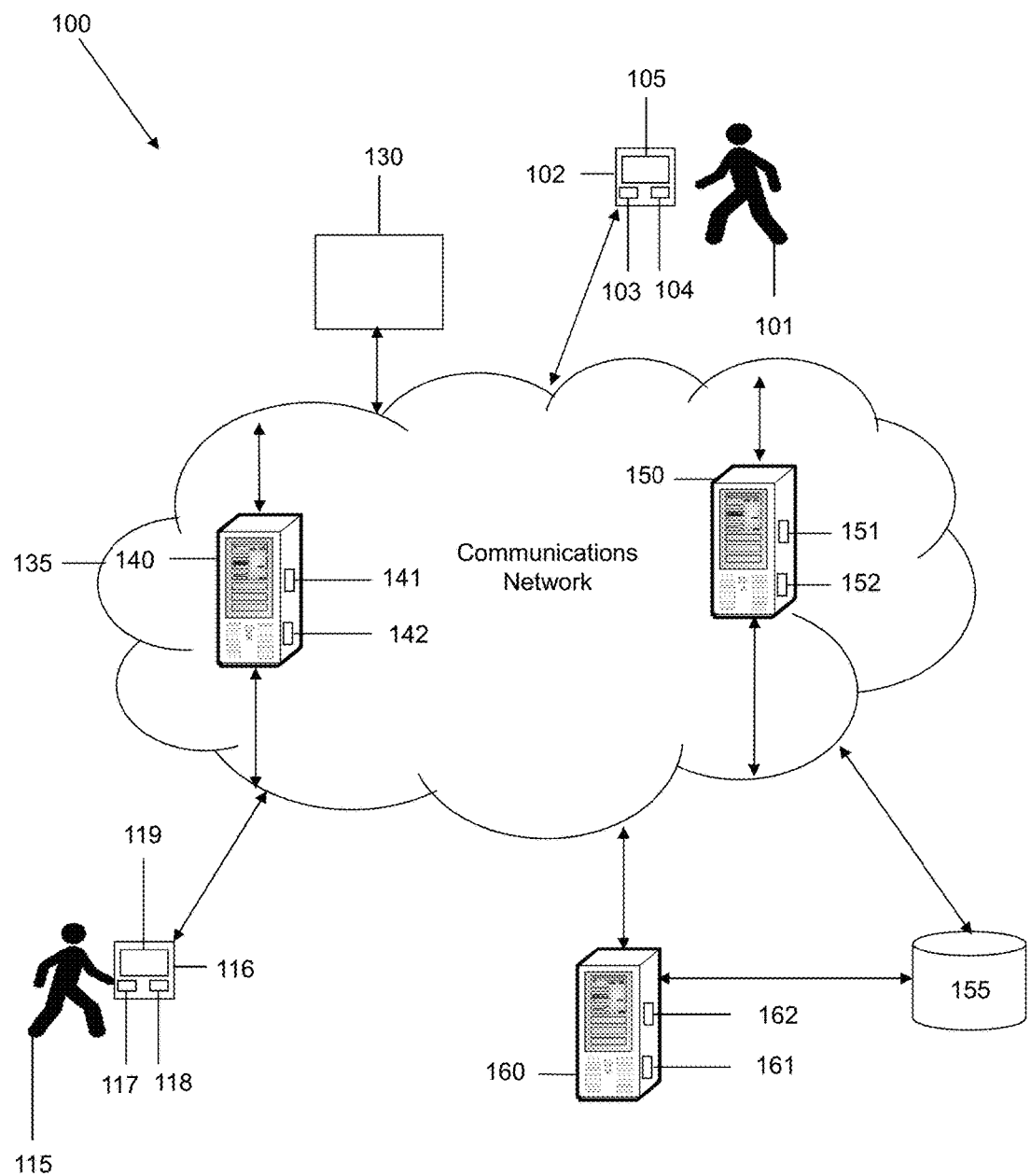
FIG. 1 is a schematic diagram of a system for manufacturing a surgical instrument according to an embodiment of the present disclosure.

A system 100 and accompanying methods for manufacturing a surgical instrument are disclosed, as shown in FIGS. 1-12. The system 100 may be configured to support internet services, software services, network services, mobile applications and services, desktop applications and services, 3D printing applications, devices, and services, and any other computing applications and services. The system may include a first user 101, who may utilize a first user device 102 to access data, content, and applications, or to perform a variety of other tasks and functions. As an example, the first user 101 may utilize first user device 102 to access a configuration program (i.e. an application) executing on the first user device 102 that may be utilized to manufacture a surgical instrument. The first user device 102 may include a memory 103 that includes instructions, and a processor 104 that executes the instructions from the memory 103 to perform the various operations that are performed by the first user device 102. In certain embodiments, the processor 104 may be hardware, software, or a combination thereof. The first user device 102 may also include an interface 105 (e.g. a screen, a monitor, a graphical user interface, etc.) that may enable the first user 101 to interact with various applications (e.g. the configuration program) executing on the first user device 102 and to interact with the system 100. In certain embodiments, the first user device 102 may be a computer, a laptop, a tablet device, a phablet, a server, a mobile device, a smartphone, a smart watch, and/or any other type of computing device. Illustratively, the first user device 102 is shown as a computer in FIG. 1.

In addition to the first user 101, the system 100 may include a second user 115, who may utilize a second user device 116 to access data, content, and applications, or to perform a variety of other tasks and functions. Much like the first user 101, the second user 115 may utilize second user device 116 to access a configuration program (i.e. an application) executing on the second user device 116 that may be utilized to manufacture a surgical instrument. The second user device 116 may include a memory 117 that includes instructions, and a processor 118 that executes the instructions from the memory 117 to perform the various operations that are performed by the second user device 116. In certain embodiments, the processor 118 may be hardware, software, or a combination thereof. The second user device 116 may also include an interface 119 (e.g. a screen, a monitor, a graphical user interface, etc.) that may enable the second user 115 to interact with various applications (e.g. the configuration program) executing on the second user device 116 and to interact with the system 100. In certain embodiments, the second user device 116 may be a computer, a laptop, a tablet device, a phablet, a server, a mobile device, a smartphone, a smart watch, and/or any other type of computing device. Illustratively, the second user device 116 is shown as a computer in FIG. 1.

The system 100 may include a 3D printer device 130, which may be configured to include any of the components and features of any type of 3D printing device. The 3D printer device 130 may be configured to create three-dimensional objects via various processes. In certain embodiments, the 3D printer device 130 may utilize its various components to form successive layers of material to create the 3D object within a particular area of the 3D printer device 130. In certain embodiments, the 3D printer device 130 may contain its own processor and memory to assist in the operations performed by the 3D printer device 130. In certain embodiments, the 3D printer device 130 may be controlled by other devices in the system 100, such as, but not limited to, the first user device 102, the second user device 116, the servers 140, 150, 160, or any combination thereof. In certain embodiments, the 3D printer device 130 may be controlled by the configuration program that is utilized to configure one or more surgical instruments. The 3D printer device 130 may be configured to receive configuration data generated based on values selected for various parameters corresponding to one or more surgical instruments. Based on the configuration data, the 3D printer device 130 may print the surgical instrument corresponding to the configuration data. Notably, the 3D printer device 130 may utilize any type of 3D printing technology to generate and print the surgical instrument or any other object.

The system 100 may also include a communications network 135. The communications network 135 of the system 100 may be configured to link each of the devices in the system 100 to one another. For example, the communications network 135 may be utilized by the first user device 102 to connect with other devices within or outside communications network 135, such as, but not limited to, the servers 140, 150, the 3D printer device 130, the second user device 116, any other device, or any combination thereof. Additionally, the communications network 135 may be configured to transmit, generate, and receive any information and data traversing the system 100. In certain embodiments, the communications network 135 may include any number of servers, databases, or other componentry. The communications network 135 may also include and be connected to a cloud-computing network, a wireless network, an Ethernet network, a satellite network, a broadband network, a cellular network, a private network, a cable network, the Internet, an internet protocol network, any network, or any combination thereof. Illustratively, servers 140 and 150 are shown as being included within communications network 135.

Notably, the functionality of the system 100 may be supported and executed by using any combination of the servers 140, 150, and 160. The servers 140, and 150 may reside in communications network 135, however, in certain embodiments, the servers 140, 150 may reside outside communications network 135. The servers 140, and 150 may be utilized to perform the various operations and functions provided by the system 100, such as those requested by applications (e.g. the configuration program) executing on the first and second user devices 102, 116. In certain embodiments, the server 140 may include a memory 141 that includes instructions, and a processor 142 that executes the instructions from the memory 141 to perform various operations that are performed by the server 140. The processor 142 may be hardware, software, or a combination thereof. Similarly, the server 150 may include a memory 151 that includes instructions, and a processor 152 that executes the instructions from the memory 151 to perform the various operations that are performed by the server 150. In certain embodiments, the servers 140, 150, and 160 may be network servers, routers, gateways, switches, media distribution hubs, signal transfer points, service control points, service switching points, firewalls, routers, edge devices, nodes, computers, mobile devices, or any other suitable computing device, or any combination thereof. In certain embodiments, the servers 140, 150 may be communicatively linked to the communications network 135, any network, any device in the system 100, or any combination thereof.

The database 155 of the system 100 may be utilized to store and relay information that traverses the system 100, cache information and/or content that traverses the system 100, store data about each of the devices in the system 100, and perform any other typical functions of a database. In certain embodiments, the database 155 may be connected to or reside within the communications network 135, any other network, or a combination thereof. In certain embodiments, the database 155 may serve as a central repository for any information associated with any of the devices and information associated with the system 100. Furthermore, the database 155 may include a processor and memory or be connected to a processor and memory to perform the various operation associated with the database 155. In certain embodiments, the database 155 may be connected to the servers 140, 150, 160, the first user device 102, the second user device 116, the 3D printer device 130, the configuration program, any devices in the system 100, any other device, any network, or any combination thereof.

The database 155 may also store information obtained from the system 100, store metadata and other information associated with the first and second users 101, 115, store communications traversing the system 100, store user preferences, store information associated with any device or signal in the system 100, store any information obtained from any of the networks in the system 100, store information relating to any devices associated with the first and second users 101, 115, or any combination thereof. In certain embodiments, the database 155 may also be configured to store any of the information relating to the surgical instruments and the specific components of the surgical instruments that have been selected by the first and/or second users 101, 115 via the configuration program, store any purchase history information relating to the surgical instruments and components of the surgical instruments, store a history of printing jobs performed by the 3D printer device 130, store the software supporting the configuration program, or any combination thereof. In certain embodiments, the database 155 may be configured to store any information generated and/or processed by the system 100, store any of the information disclosed for any of the operations and functions disclosed for the system 100 herewith, store any information traversing the system 100, or any combination thereof. Furthermore, the database 155 may be configured to process queries sent to it by any device in the system 100.

Notably, as shown in FIG. 1, the system 100 may perform any of the operative functions disclosed herein by utilizing the processing capabilities of server 160, the storage capacity of the database 155, or any other component of the system 100 to perform the operative functions disclosed herein. The server 160 may include one or more processors 162 that may be configured to process any of the various functions of the system 100. The processors 162 may be software, hardware, or a combination of hardware and software. Additionally, the server 160 may also include a memory 161, which stores instructions that the processors 162 may execute to perform various operations of the system 100. For example, the server 160 may assist in processing loads handled by the various devices in the system 100, such as, but not limited to, receiving inputs corresponding to values selected for one or more parameters of a surgical instrument; determining if the values for the one or more parameters have been received; generating configuration data from the values for the one or more parameters; transferring the configuration data to the 3D printer device 130; printing the surgical instrument by utilizing the 3D printer device 130; and performing any other suitable operations conducted in the system 100 or otherwise. In one embodiment, multiple servers 160 may be utilized to process the functions of the system 100. The server 160 and other devices in the system 100, may utilize the database 155 for storing data about the devices in the system 100 or any other information that is associated with the system 100. In one embodiment, multiple databases 155 may be utilized to store data in the system 100.

Although FIG. 1 illustrates a specific example configuration of the various components of the system 100, the system 100 may include any configuration of the components, which may include using a greater or lesser number of the components. For example, the system 100 is illustratively shown as including a first user device 102, a second user device 116, a 3D printer device 130, a communications network 135, a server 140, a server 150, a server 160, and a database 155. However, the system 100 may include multiple first user devices 102, multiple second user devices 116, multiple 3D printer devices 130, multiple communications networks 135, multiple servers 140, multiple servers 150, multiple servers 160, multiple databases 155, or any number of any of the other components inside or outside the system 100. Furthermore, in certain embodiments, substantial portions of the functionality and operations of the system 100 may be performed by other networks and systems that may be connected to system 100.

Figure 2:
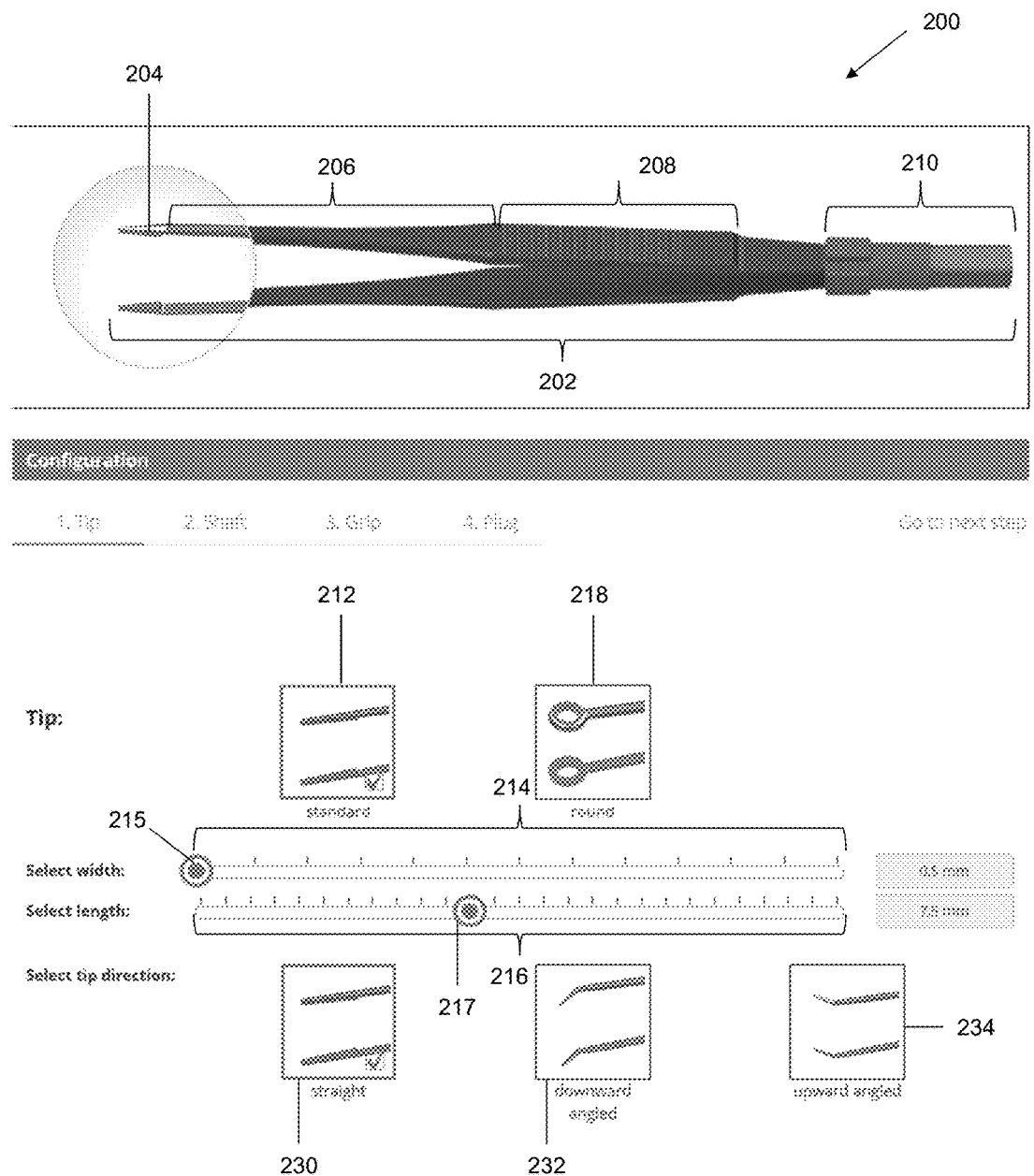
FIG. 2 is a schematic diagram of a graphical user interface of a configuration program of the system of FIG. 1, which enables the selection of different types of tips for a surgical instrument, different widths and lengths of the surgical instrument, and various tip directions for the surgical instrument, and which illustrates a graphical representation of a standard tip for the surgical instrument.

Operatively, in an example scenario, the system 100 may include presenting, to the first user 101, a graphical user interface (GUI) 200 of a configuration program for creating a surgical instrument, as shown in FIG. 2. The GUI 200 may be presented on the interface 105 of first user device 102 and may present a default graphical representation of a surgical instrument 202, along with various options for configuring the surgical instrument 202. On GUI 200 of the configuration program, the first user 101 may be given the option to select the type of tip 204 or working end for the surgical instrument he or she desires to create. For example, in GUI 200, the options of selecting a standard tip 212 and a round tip 218 may provided. If the first user 101 selects the standard tip 212, the graphical representation of the surgical instrument 202 may be updated in real-time to reflect the selection of the standard tip 212. Additionally, after selection of the standard tip 212, the GUI 200 may display an option for selecting a value for a parameter of the standard tip 212, such as a width of the standard tip 212. The width of the standard tip 212 may be selected via range slider 215 that is configured to allow the first user 101 to select a value for the width between a range of values presented on a bar 214. In certain embodiments, a specific value of an infinite number of different values may be selected via the range slider 215 when the first user 101 causes the range slider 215 to traverse the bar 214 on the GUI 200. In certain embodiments, the possible values on the bar 214 may increase at certain increments as the first user 101 causes the range slider 215 to traverse the bar 214. For example, in GUI 200, the bar 214 allows for the values to increase or decrease by 0.5 mm increments or any other desired increments.

Furthermore, the GUI 200 may display the option for selecting the length of the standard tip 212. The length of the standard tip 212 may be selected via range slider 217 that is configured to allow the first user 101 to select a value for the length between a range of values presented on a bar 216. In certain embodiments, a specific value of an infinite number of different values may be selected via the range slider 217 when the first user 101 causes the range slider 217 to traverse the bar 216 on the GUI 200. In certain embodiments, the possible values on the bar 216 may increase at certain increments as the first user 101 causes the range slider 217 to traverse the bar 216. For example, in GUI 200, the bar 216 allows for the values to increase or decrease by millimeter increments. The GUI 200 may also display options for selecting the tip direction for the tip 204 for the surgical instrument. For example, in certain embodiments, the tip direction may be a straight tip direction 230, a downward angled tip direction 232, and an upward angled tip direction 234. Depending on which tip direction is selected by the first user 101, the graphical representation of the surgical instrument 202 may be updated to reflect the tip direction selection.

Figure 3:
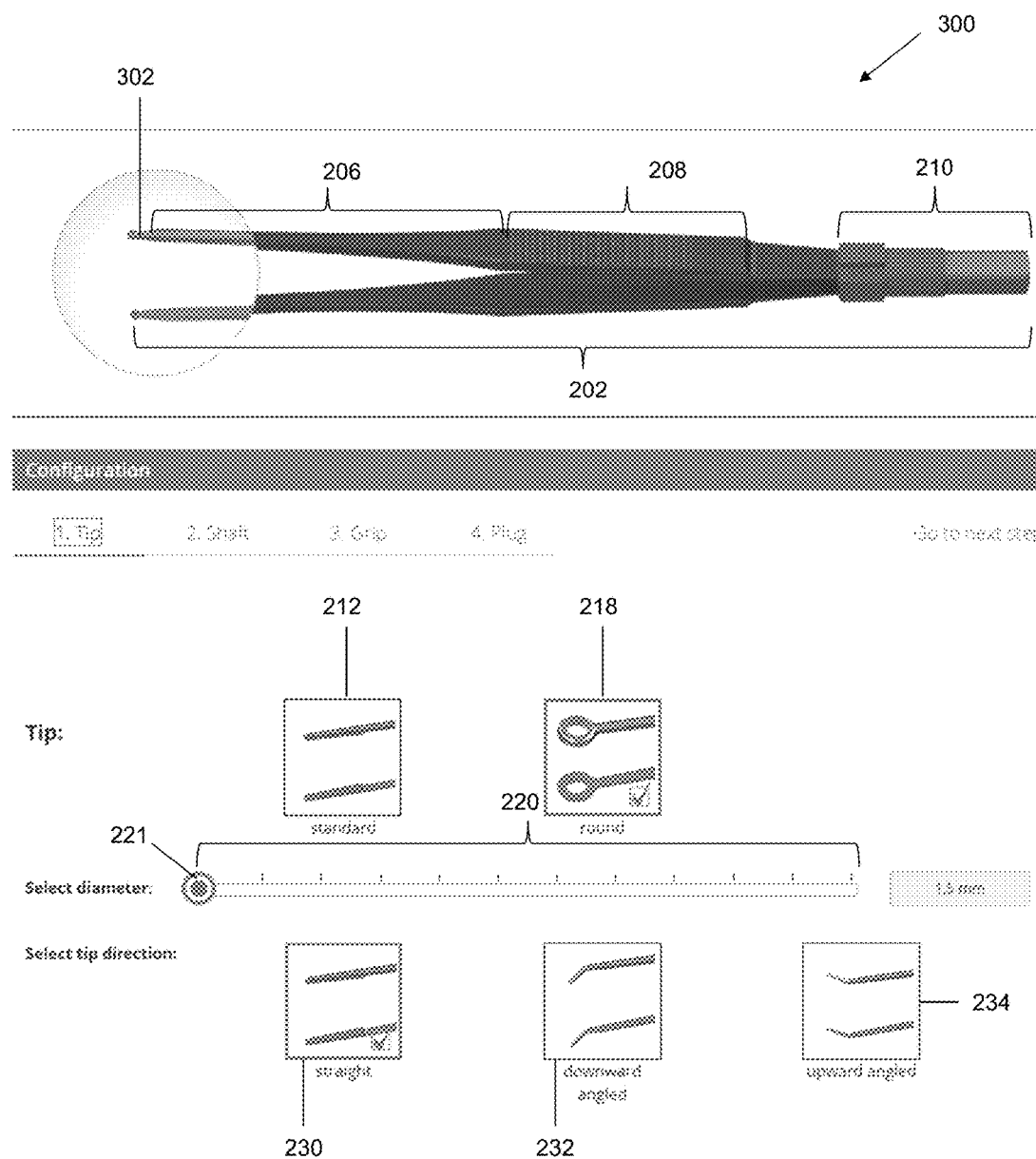
FIG. 3 is a schematic diagram of a graphical user interface of a configuration program of the system of FIG. 1, which enables the selection of different types of tips for a surgical instrument, different widths and lengths of the surgical instrument, and various tip directions for the surgical instrument, and which illustrates a graphical representation of a rounded tip for the surgical instrument.

If the first user 101 decides to select round tip 218 instead of standard tip 212, GUI 300 may be displayed on the first user device 102, as shown in FIG. 3. The graphical representation of the surgical instrument 202 may be updated in real-time to reflect the selection of the round tip 218. Additionally, after selection of the round tip 218, the GUI 300 may display an option for selecting a value for a parameter of the round tip 218, such as a diameter of the round tip 218. The diameter of the round tip 218 may be selected via range slider 221 that is configured to allow the first user 101 to select a value for the diameter between a range of values presented on a bar 220. In certain embodiments, a specific value of an infinite number of different values may be selected via the range slider 221 when the first user 101 causes the range slider 221 to traverse the bar 220 on the GUI 300. In certain embodiments, the possible values on the bar 220 may increase at certain increments as the first user 101 causes the range slider 221 to traverse the bar 220. For example, in GUI 300, the bar 220 may allow for the values to increase or decrease by 1.5 mm increments or any other desired increments. The GUI 300 may also display options for selecting the tip direction for the tip 204 for the surgical instrument. For example, in certain embodiments, the tip direction may be a straight tip direction 230, a downward angled tip direction 232, and an upward angled tip direction 234. Depending on which tip direction is selected by the first user 101, the graphical representation of the surgical instrument 202 may be updated to reflect the tip direction selection in GUI 300.

Figure 4:
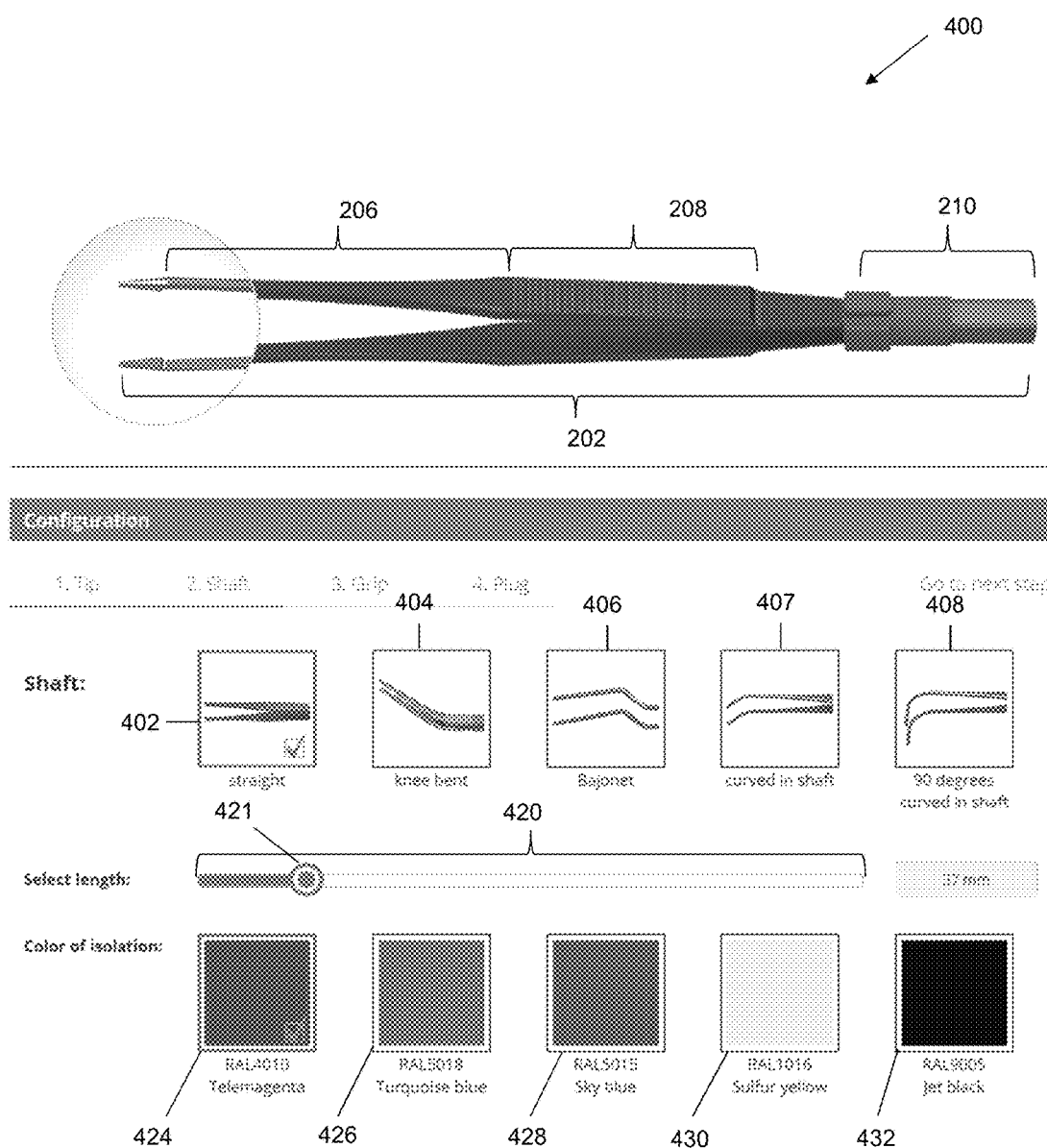
FIG. 4 is a schematic diagram of a graphical user interface of a configuration program of the system of FIG. 1, which enables the selection of different types of shafts for a surgical instrument, different lengths for the shaft, and different colors for insulating coatings for the surgical instrument.

Once the tip 204 is selected by the first user 101, the GUI 400 may be displayed on the first user device 102, as shown in FIG. 4. The GUI 400 may present options corresponding to the shaft 206 of the surgical instrument. In certain embodiments, the options may include, but are not limited to, a straight shaft option 402, a knee bent option 404, a Bajonet option 406, a curved-in-shaft option 407, a 90 degrees curved in shaft option 408, among other options. For example, if the first user 101 selects the straight shaft option 402, the graphical representation of the surgical instrument 202 may be updated in real-time and the configuration program may provide the option to select the length of the shaft 206. The length of the shaft 206 may be selected via range slider 421 that is configured to allow the first user 101 to select a value for the length between a range of values presented on a bar 420. In certain embodiments, a specific value of an infinite number of different values may be selected via the range slider 421 when the first user 101 causes the range slider 421 to traverse the bar 420 on the GUI 400. In certain embodiments, the possible values on the bar 420 may increase at certain increments as the first user 101 causes the range slider 421 to traverse the bar 420. For example, in GUI 400, the bar 420 allows for the values to increase or decrease by millimeter increments. The GUI 400 may also allow for the selection of the material, and/or a color for insulation for the surgical instrument. For example, the GUI 400 may provide a telemagenta option 424, a turquoise blue option 426, a sky blue option 428, a sulfur yellow option 430, and a jet black 432 option. Based on what the first user 101 selects for the color and/or material, the graphical representation of the surgical instrument 202 may be updated accordingly.

Figure 5:
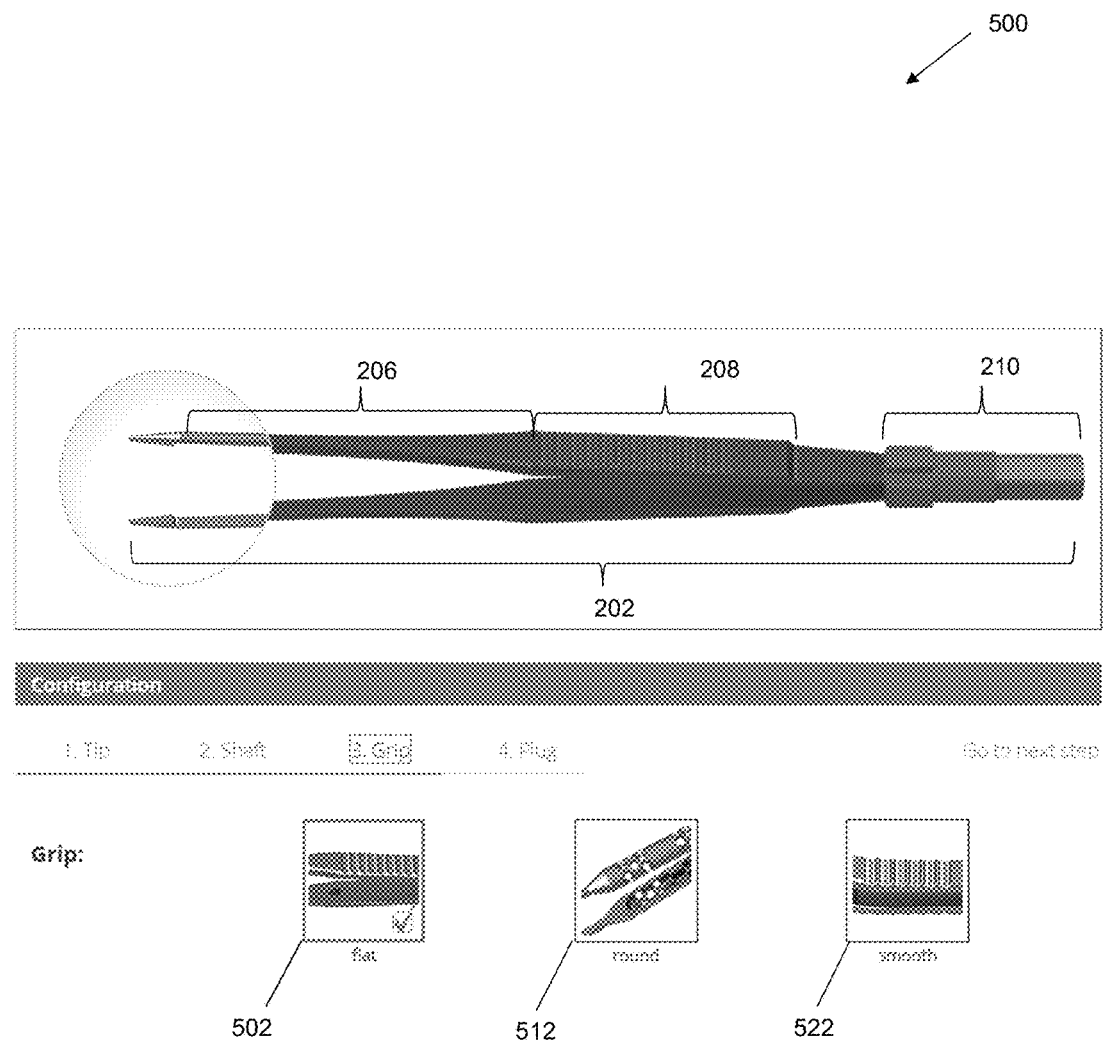
FIG. 5 is a schematic diagram of a graphical user interface of a configuration program of the system of FIG. 1, which enables the selection of different types of grips for a surgical instrument and which illustrates a graphical representation of a flat grip on a graphical representation of the surgical instrument.
Figure 6:
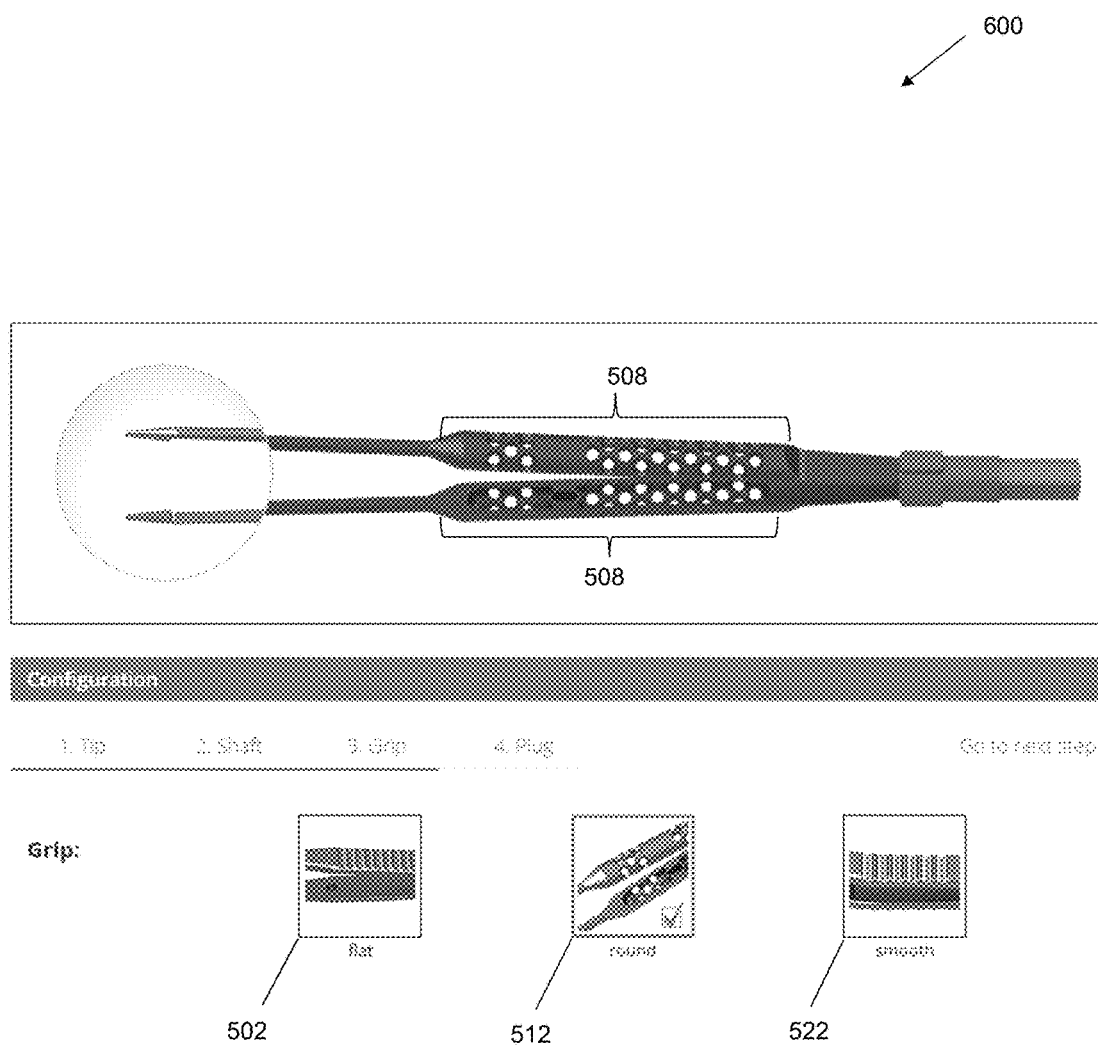
FIG. 6 is a schematic diagram of a graphical user interface of a configuration program of the system of FIG. 1, which enables the selection of different types of grips for a surgical instrument and which illustrates a graphical representation of a round grip on a graphical representation of the surgical instrument.
Figure 7:
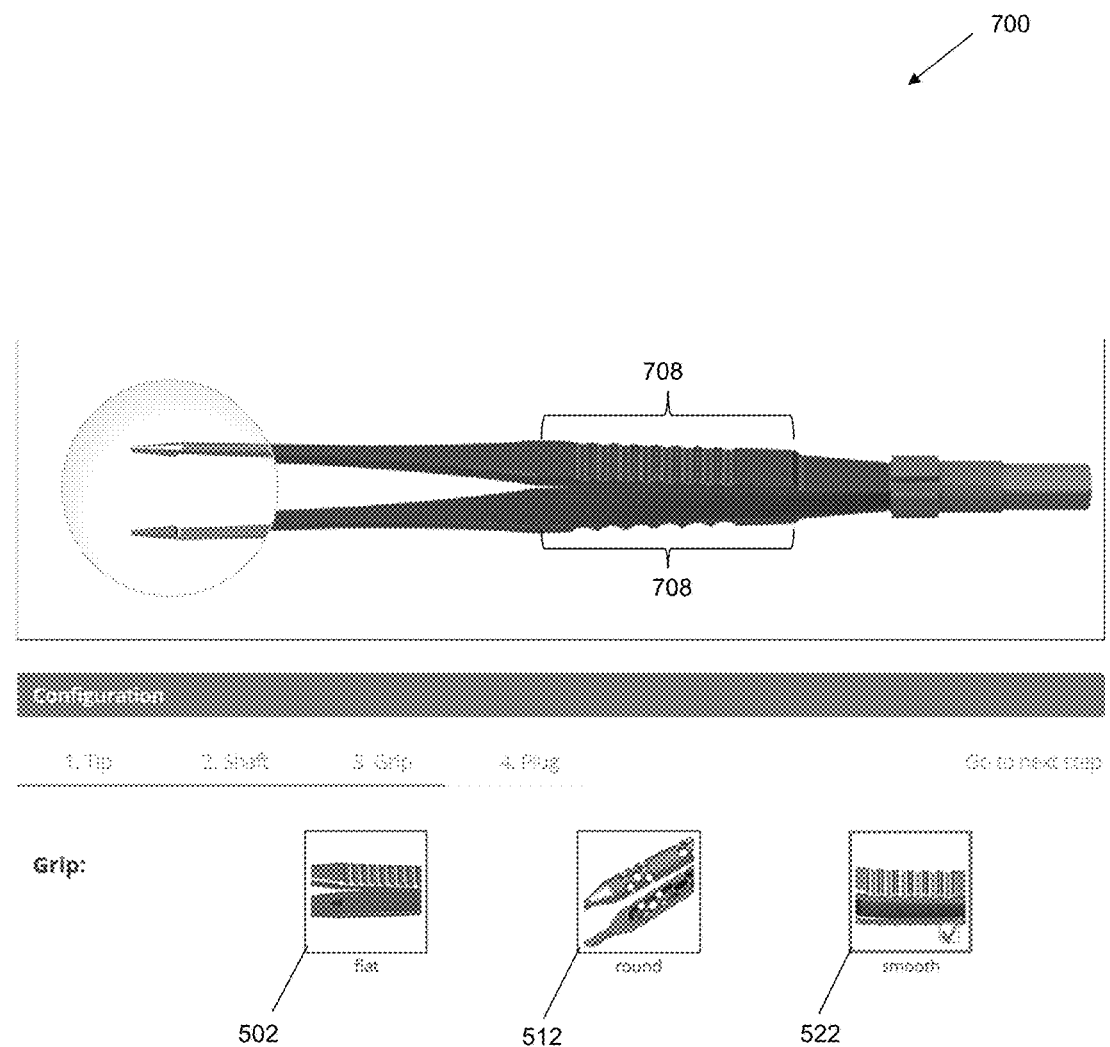
FIG. 7 is a schematic diagram of a graphical user interface of a configuration program of the system of FIG. 1, which enables the selection of different types of grips for a surgical instrument and which illustrates a graphical representation of a smooth grip on a graphical representation of the surgical instrument.

Once the shaft parameters are selected by the first user 101, the GUI 500 may be displayed on the first user device, as shown in FIG. 5. The GUI 500 may present options corresponding to the grip 208 of the surgical instrument. In certain embodiments, the options may include, but are not limited to, a flat grip option 502, a round grip option 512, and a smooth grip option 522, among other options. For example, if the first user 101 selects the flat grip option 502, the graphical representation of the surgical instrument 202 may be updated in real-time and may depict the surgical instrument as having the flat grip option 502, as shown in FIG. 5. If, however, the first user 101 selects the round grip option 512, the graphical representation of the surgical instrument 202 may be updated in real time to reflect the selection, as shown in GUI 600 of FIG. 6. Still further, if the first user 101 selects the smooth grip option 522, the graphical representation of the surgical instrument 202 may be updated in real time to reflect the selection of the smooth grip option 522, as shown in GUI 700 of FIG. 7.

Figure 8:
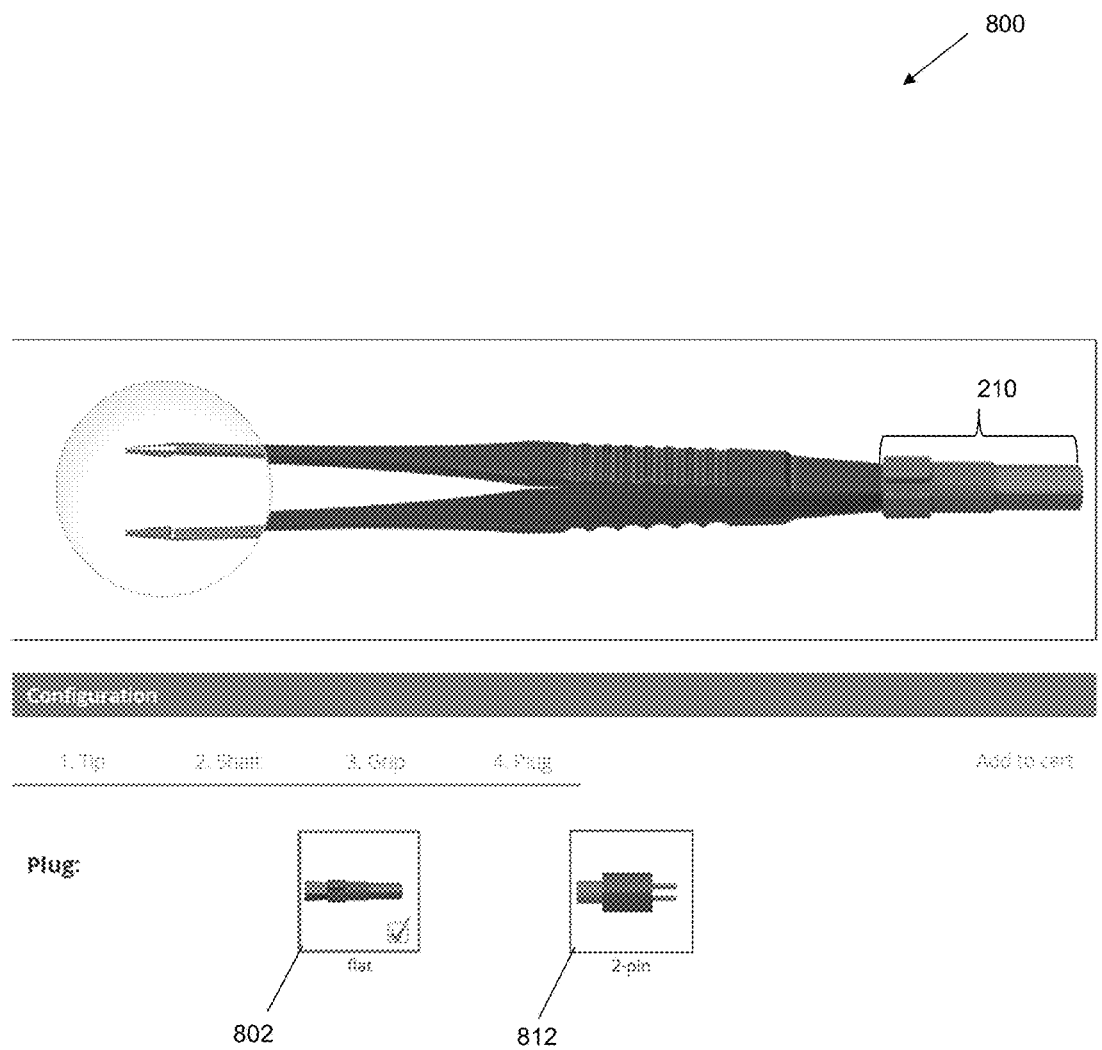
FIG. 8 is a schematic diagram of a graphical user interface of a configuration program of the system of FIG. 1, which enables the selection of different types of electrical connections for use with a surgical instrument and which illustrates a graphical representation of a flat electrical connection type on a graphical representation of the surgical instrument.
Figure 9:
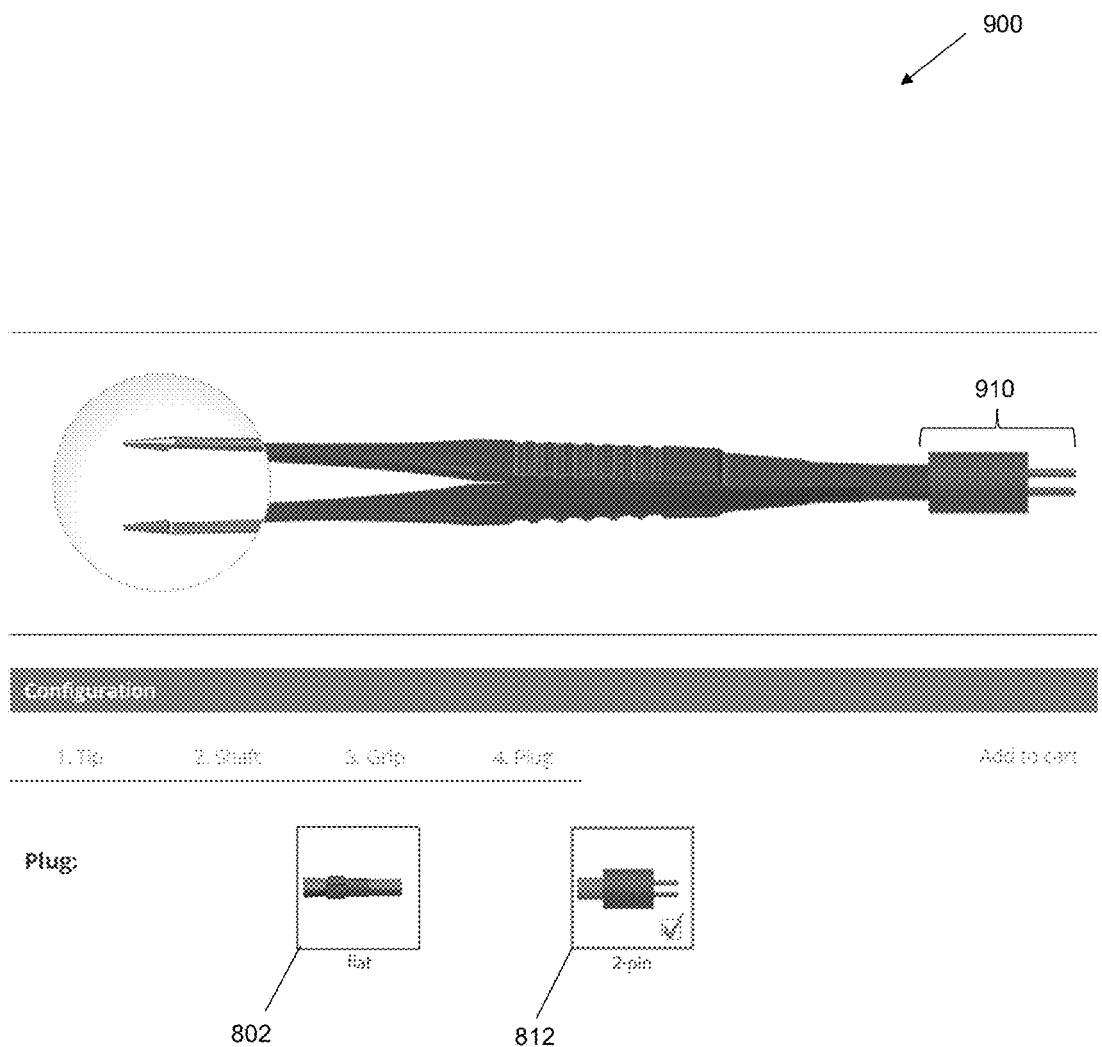
FIG. 9 is a schematic diagram of a graphical user interface of a configuration program of the system of FIG. 1, which enables the selection of different types of electrical connections for use with a surgical instrument and which illustrates a graphical representation of a 2-pin electrical connection type on a graphical representation of the surgical instrument.
Figure 10A:
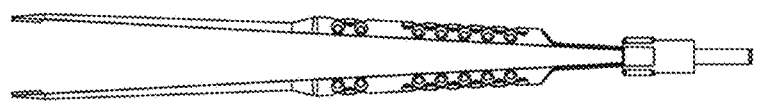
FIG. 10A is a diagram of a left side view of a sample surgical instrument manufactured by the system of FIG. 1.
Figure 10B:
FIG. 10B is a diagram of a top view of a sample surgical instrument manufactured by the system of FIG. 1.
Figure 10C:
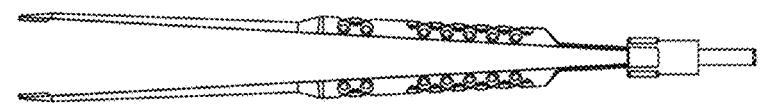
FIG. 10C is a diagram of a right side view of a sample surgical instrument manufactured by the system of FIG. 1.
Figure 10D:
FIG. 10D is a diagram of a back view of a sample surgical instrument manufactured by the system of FIG. 1.
Figure 10E:
FIG. 10E is a diagram of a front view of a sample surgical instrument manufactured by the system of FIG. 1.
Figure 10F:
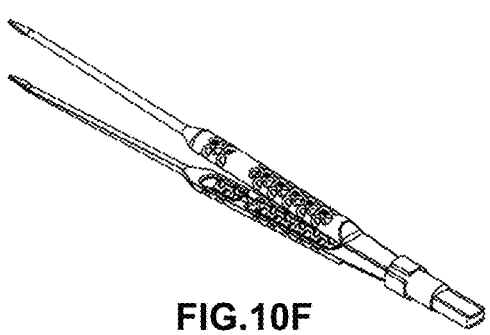
FIG. 10F is a diagram of an isometric view of a sample surgical instrument manufactured by the system of FIG. 1.
Figure 10G:
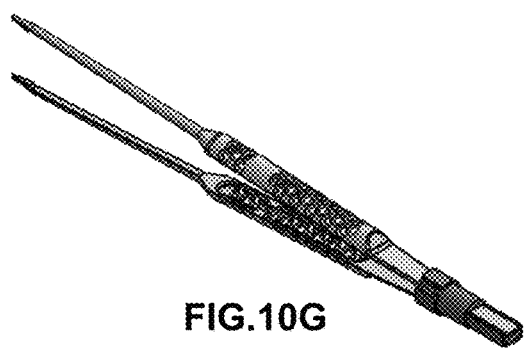
FIG. 10G is a diagram of another isometric view of a sample surgical instrument manufactured by the system of FIG. 1.

Once the first user 101 selects the parameters for the grip of the surgical instrument, the configuration program may display GUI 800. GUI 800 may present options corresponding to the type of electrical connection 210 to be utilized with the surgical instrument. In certain embodiments, the options may include, but are not limited to, a flat electrical connection option 802 and a 2-pin electrical connection option. If the first user 101 selects the flat electrical connection option 802, the graphical representation of the surgical instrument 202 may be updated to reflect the flat electrical connection option 802, as shown in FIG. 8. If, however, the first user 101 selects the 2-pin electrical connection option 812, the graphical representation of the surgical instrument 202 may be updated to reflect the 2-pin electrical connection option 812, as shown in GUI 900 of FIG. 9. Once all the various options corresponding to the parameters of the surgical instrument are selected by the first user 101 via the configuration program, the selected values may be utilized by the configuration program to generate configuration data corresponding to the surgical instrument and which may be in a format readable by the 3D printer device 130. The configuration data may be transmitted to the 3D printer device 130, and the 3D printer device 130 may proceed to create the surgical instrument by any desired 3D printing process that the 3D printer device 130 is capable of using. FIGS. 10A-10G illustrate a sample surgical instrument that may be created by the 3D printer device 130 and various angles and orientations of the surgical instrument.

In certain embodiments, advantageously, the surgical instrument to be manufactured has at least one handle (e.g. grip 208) and at least one working end (e.g. tip 302), and the at least one parameter originates from a group of parameters comprising at least a subset of the following parameters: shape of the working end, length of the working end, width of the working end, thickness of the working end, shape of the handle, length of the handle, width of the handle, and/or thickness of the handle. This makes it possible to adapt the shape and size of the working end specially to the specific use of the surgical instrument in the context of a certain operation while also taking the anatomy of the user of the surgical instrument into account.

Advantageously, the value of the parameter of the shape of the working end can be selected from a group of values comprising at least a subset of the following values: triangular, rectangular, round, or oval-shaped.

The value of the parameter of the length, width, and/or thickness of the working end can be advantageously selected from a group of values comprising at least one specific value, advantageously a range between two specific values from within which the value can be selected, preferably set in an infinitely variable manner. The configuration program can thus predefine one or more specific values for the length, width, and/or thickness of the working end, for example, from which the user can select a value. In order to afford the user the greatest possible design flexibility so that he can adapt the surgical instrument to his own requirements and to the requirements of the operation, the value can preferably be set in an infinitely variable manner between two specific values. In relation to the present disclosure, "infinitely variable" means that a selection can be made of the values within a predetermined system of increments which corresponds, for example, to the tolerance range of the values. A system with increments of 0.5, 0.25 or 0.1 mm is conceivable, for example.

Advantageously, the value of the parameter of the shape of the handle can be selected from a group of values comprising at least a subset of the following values: flat, half shell-shaped, flat with holes, or half shell-shaped with holes.

According to a preferred embodiment, the value of the parameter of the length, width, and/or thickness of the handle can be advantageously selected from a group of values comprising at least one specific value, advantageously a range between two specific values from within which the value can be selected, preferably set in an infinitely variable manner. The configuration program can thus predefine one or more specific values for the length, width, and/or thickness of the handle, for example, from which the user can select a value. In order to afford the user the greatest possible design flexibility so that he can adapt the surgical instrument to his own requirements and to the requirements of the operation, the value can preferably be set in an infinitely variable manner between two specific values.

Advantageously, the surgical instrument to be manufactured has at least one shaft, and the group of parameters additionally comprises at least the following parameters: shape of the shaft, length of the shaft, width of the shaft, and/or thickness of the shaft.

Preferably, the value of the parameter of the shape of the shaft can be selected from a group of values comprising at least a subset of the following values: straight, curved, angled, or doubly angled.

Preferably, the value of the parameter of the length, width, and/or thickness of the shaft can be selected from a group of values comprising at least one specific value, advantageously a range between two specific values from within which the value can be selected, preferably set in an infinitely variable manner. The configuration program can thus predefine one or more specific values for the length, width, and/or thickness of the shaft, for example, from which the user can select a value. In order to afford the user the greatest possible design flexibility so that he can adapt the surgical instrument to his own requirements and to the requirements of the operation, the value can be preferably be set in an infinitely variable manner between two specific values.

According to a preferred exemplary embodiment, the surgical instrument is printed in an electrically conductive material by means of the 3D printer device 130. For example, the surgical instrument can be printed in an electrically conductive metal.

A preferred embodiment of the disclosure makes a provision that the method further comprises the following step: selection of a material and/or a color for an insulating coating for portions of the surgical instrument. Advantageously, the insulating coating is applied to the surgical instrument in another method step, for example either by the 3D printer device 130 or by spraying.

An especially preferred embodiment of the disclosure makes a provision that the surgical instrument is a monopolar or bipolar coagulation forceps. Particularly for such coagulation forceps, the conventional manufacturing methods are especially cost-intensive. Since a much smaller quantity of coagulation forceps is usually needed in comparison to other forceps, the convention has been to produce series with small unit quantities that are sold off over a longer period of time. For economic reasons, it is generally not profitable to keep a large number of different types of coagulation forceps on hand, since only small quantities are needed. However, this puts the user in the problematic position that coagulation forceps that are optimally suited to the operation to be performed are often not available. By means of the method according to the disclosure, the user can be provided with coagulation forceps that are optimally adapted to the requirements of the operation and of the user.

If the surgical instrument is coagulation forceps, an advantageous development of the method makes a provision that, in another step, the type of electrical connection is selected, in which case a choice can be made between a connector for a flat cable or for a two-pin plug, for example.

Alternatively, the surgical instrument is advantageously embodied as a hook or retractor, particularly for breast surgery, since it has not made much economic sense until now to keep a wide variety of different types of such hooks and retractors on hand, either, due to the relatively small quantities needed.

An especially preferred embodiment of the method according to the disclosure makes a provision that the configuration program uses the currently selected data to generate a graphic representation of the surgical instrument corresponding to the currently selected data and displays it graphically, particularly on a screen. This enables a user of the configuration program to identify at any time how he has currently configured his surgical instrument.

A surgical instrument according to the disclosure is manufactured by means of an inventive method as described above and is particularly embodied as monopolar or bipolar coagulation forceps or as a hook or retractor.

An exemplary embodiment of the disclosure is described in detail below.

For example, the method for manufacturing a surgical instrument can proceed as follows:

A user who requires, to the greatest possible extent, a surgical instrument that is maximally adapted to his needs starts the configuration program, which can be accessed on an internet platform, for example. If it is possible to choose between different types of surgical instrument, he first selects the type of surgical instrument that he requires—for example, a retractor or forceps, particularly monopolar or bipolar coagulation forceps.

In the configuration program, a value is then selected for at least one parameter of the surgical instrument. For example, the user can select the value for at least one of the following parameters for monopolar or bipolar coagulation forceps: shape of the working end, size of the working end, shape of the handle, size of the handle, shape of the shaft, size of the shaft. In the configuration program, the parameters for which the user can choose values are displayed. The user can choose values for the corresponding parameters in any order.

For example, if a value must be selected for the parameter of the shape of the working end, the user can first activate the selection of the value for the parameter of the shape of the working end and then choose the value from a group of values comprising at least a subset of the following values: triangular, rectangular, round, oval-shaped. For example, it can be indicated to the user that he can select between the shapes triangular, rectangular or round. The user can opt for a rectangular working end, for example.

In another step, the user can choose a value for the parameter of the size of the working end. The size of the working end can include the parameters of the length of the working end, the width of the working end and/or the thickness of the working end. Each of these parameters can be chosen in a separate selection step. In the configuration program, a group of values can be stored for each one of these parameters from which the user can choose a value. The group of values comprises at least one specific value, for example several discrete values, or, especially preferably, a range between two specific values within which the value can be selected, preferably in infinitely variable fashion. For instance, if the user would like to set the length of the working end, the configuration program could offer him a choice between a length of 2 mm, 5 mm, 10 mm or 20 mm, for example. Alternatively, the configuration program could indicate a range from 1 to 20 mm within which the user can select the range, preferably set the range in infinitely variable fashion. An infinitely variable setting can take the form of a system of increments predefined by the configuration program, for example in intervals of 0.5 mm, 0.25 mm, or 0.1 mm. The user is thus able to select a value of 8.5 mm for the parameter of the length of the working end, for example. The same also applies to the choice of a value for the width of the working end and/or the choice of a value for the thickness of the working end. In the case of a round working end, for example, the radius of the working end could be indicated as a parameter, in which case the configuration program indicates one or more discrete values from which the user can make a selection, or, alternatively, indicates a range between two values within which the user can select the radius in the framework of fixed increments.

Preferably, the user can also choose the values for the shape of the handle and/or the size of the handle, particularly the length, width, and/or thickness of the handle. If the user wishes to choose a value for the parameter of the shape of the handle, he first advantageously activates this selection and can then choose the value of the parameter from a group of values comprising at least a subset of the following values, for example: flat, half shell-shaped, flat with holes, half shell-shaped with holes. For example, the user can opt for a flat handle that particularly has no holes. Furthermore, the user can choose values for the length, width, and/or thickness of the handle from a group of values comprising at least one specific value, advantageously a range between two specific values from within which the value can be selected, preferably set in an infinitely variable manner. The previous remarks concerning the selection of the values of the parameter of the length, width, and/or thickness of the working end are applicable to the selection of the parameter of the length, width, and/or thickness of the handle as well.

Preferably, the user can also choose values for the parameters of the shape of the shaft and/or the size of the shaft, particularly the length, width, and/or thickness of the shaft. If the value of the parameter of the shape of the shaft is to be selected, it can be selected from a group of values comprising at least a subset of the following values, for example: straight, curved, angled, doubly angled. The previous remarks concerning the selection of the values for the length, width, and/or thickness of the working end or of the handle are also applicable to the selection of the parameter of the length, width, and/or thickness of the shaft.

The material in which the surgical instrument is printed can either already be set—for example, as a certain metal—or advantageously also chosen by the user in another selection step.

In an automated manner according to the disclosure, the configuration program generates configuration data based on the selected values. In a preferred embodiment, a graphic representation of the surgical instrument corresponding to the currently selected values is additionally generated on the basis of the currently selected values for the various parameters and displayed graphically, particularly on a screen. The user is thus able at any time to see the surgical instrument that he has currently configured.

Once the user finishes choosing the values for the parameters, configuration data are generated in an automated manner by the configuration program from the selected values. These data are then transferred to a 3D printer. This can occur, for example, when the user of the configuration program orders the surgical instrument configured in this way in an ordering process. The surgical instrument is then printed out by means of the 3D printer and preferably shipped to the user.

If an insulating coating of at least portions of the surgical instrument is desired, the insulation, the material, and/or a color for the insulation can be chosen in another selection step. The application of the insulating coating to the surgical instrument can be performed, for example, either by the 3D printer device 130 or in a method step subsequent to the 3D printing, for example by spraying.

If the selected surgical instrument is monopolar or bipolar coagulation forceps, the user can also be given the opportunity in the configuration program to choose between various electrical connections for the coagulation forceps, for example between a connector for a flat cable or a two-pin plug. This electrical connector can be applied to the surgical instrument in another method step either by the 3D printer device 130 or in a method step subsequent to the 3D printing.

Figure 11:
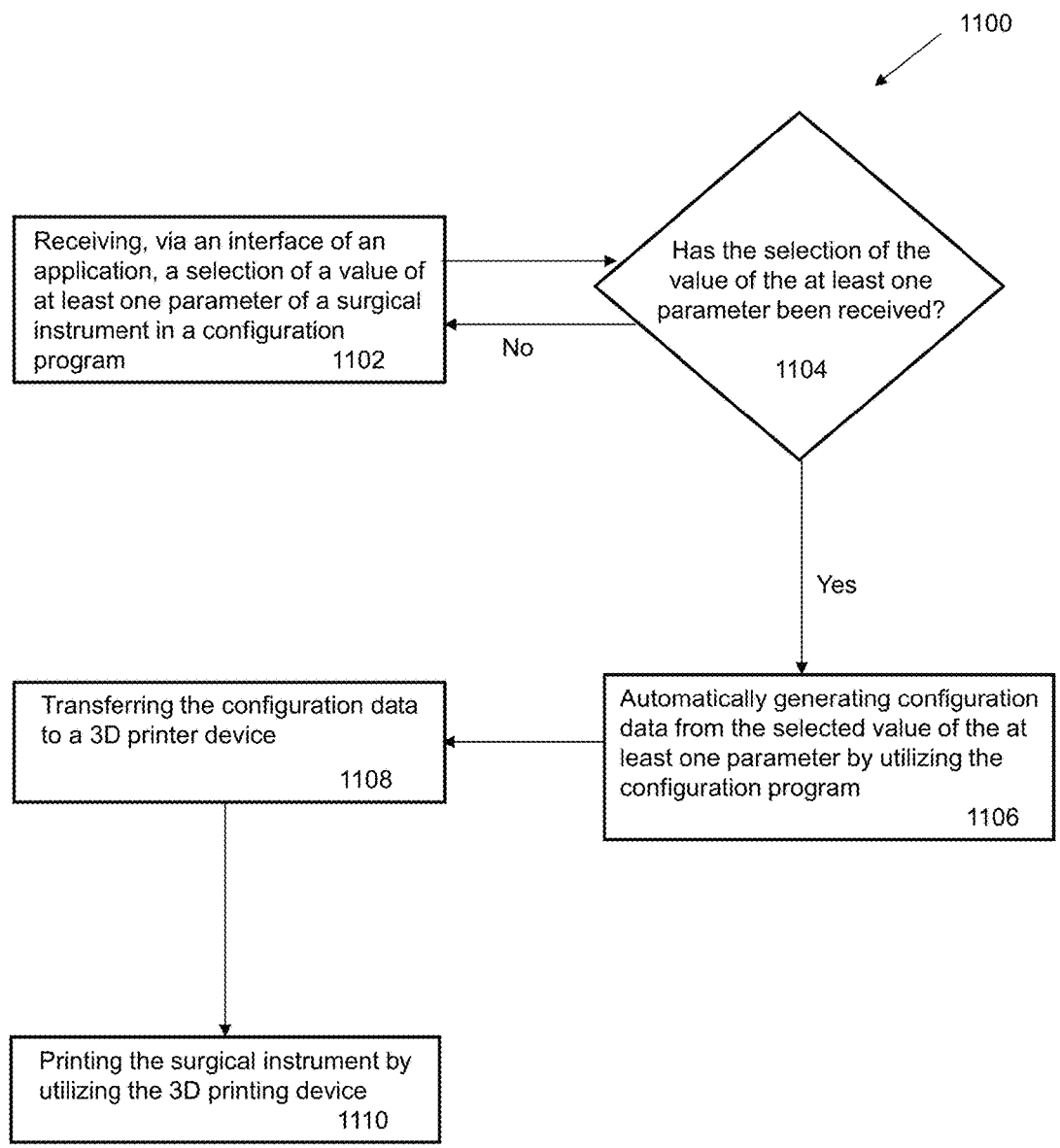
FIG. 11 is a flow diagram illustrating a sample method for manufacturing a surgical instrument according to an embodiment of the present disclosure.

Now referring to FIG. 11, an method 1100 for manufacturing a surgical instrument according to the present disclosure is disclosed. The method 1100 may include and incorporate any of the features and functionality of the system 100 and methods described herein, such as those described above. Additionally, the method 1100 may utilize any of the devices in the system 100 or as otherwise described herein to accomplish the steps of the method 1100. The method 1100 may begin at step 1102, which may include receiving, via an interface of an application, a selection of a value of at least one parameter of a surgical instrument in a configuration program. At step 1104, the method 1100 may include determining if the selection of the value of the at least one parameter has been received. If not, the method 1100 may revert back to step 1102 until a value of at least one parameter for the surgical instrument is received. If the value of the at least one parameter is received, the method 1100 may proceed to step 1106, which may include automatically generating configuration data from the selected value of the at least one parameter by utilizing the configuration program. Once the configuration data is generated, the method 1100 may proceed to step 1108, which may include transferring the configuration data to a 3D printer device, such as 3D printer device 130. Once the configuration data is transferred to the 3D printer device 130, the method 1100 may include printing the surgical instrument by utilizing the 3D printer device 130, at step 1110.

The functionality steps and provided by the steps and methods described herein enable the 3D printer device 130 to generate and create 3D objects, such as surgical instruments, with greater efficiency than previously existing technologies. This is particularly true based on the rapid generation of configuration data from the selected values of the parameters input into the configuration program.

Figure 12:
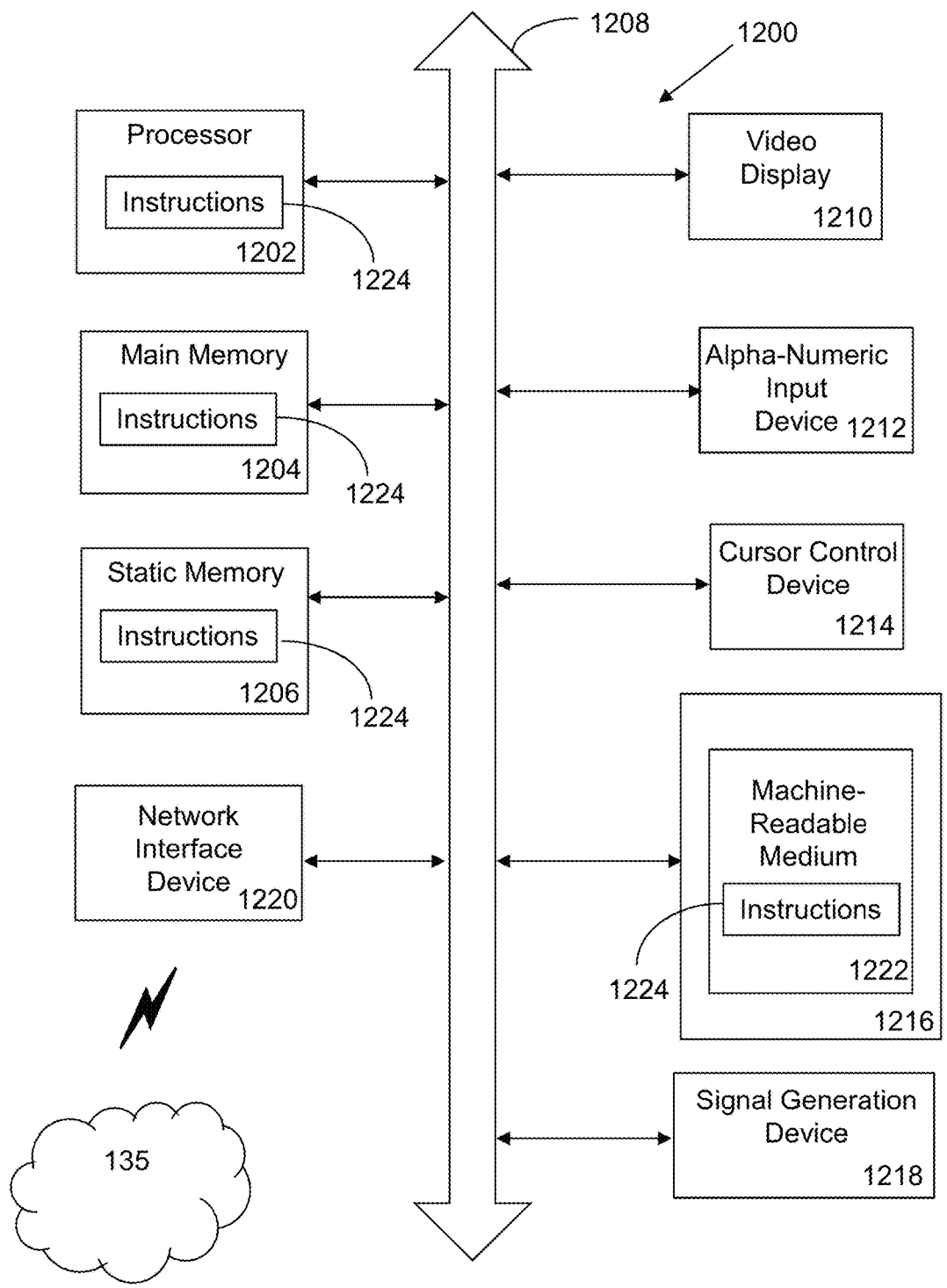
FIG. 12 is a schematic diagram of a machine in the form of a computer system within which a set of instructions, when executed, may cause the machine to perform any one or more of the methodologies or operations of the systems and methods for manufacturing a surgical instrument.

Referring now also to FIG. 12, at least a portion of the methodologies and techniques described with respect to the exemplary embodiments of the system 100 and methods can incorporate a machine, such as, but not limited to, computer system 1200, or other computing device within which a set of instructions, when executed, may cause the machine to perform any one or more of the methodologies or functions discussed above. The machine may be configured to facilitate various operations conducted by the system 100. For example, the machine may be configured to, but is not limited to, assist the system 100 by providing processing power to assist with processing loads experienced in the system 100, by providing storage capacity for storing instructions or data traversing the system 100, or by assisting with any other operations conducted by or within the system 100.

In some embodiments, the machine may operate as a standalone device. In some embodiments, the machine may be connected (e.g., using communications network 135, another network, or a combination thereof) to and assist with operations performed by other machines and systems, such as, but not limited to, the first user device 102, the second user device 106, the 3D printer device 130, the server 140, the server 150, the database 155, the server 160, or any combination thereof. The machine may be connected with any component in the system 100. In a networked deployment, the machine may operate in the capacity of a server or a client user machine in a server-client user network environment, or as a peer machine in a peer-to-peer (or distributed) network environment. The machine may comprise a server computer, a client user computer, a personal computer (PC), a tablet PC, a laptop computer, a desktop computer, a control system, a network router, switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The computer system 1200 may include a processor 1202 (e.g., a central processing unit (CPU), a graphics processing unit (GPU, or both), a main memory 1204 and a static memory 1206, which communicate with each other via a bus 1208. The computer system 1200 may further include a video display unit 1210, which may be, but is not limited to, a liquid crystal display (LCD), a flat panel, a solid state display, or a cathode ray tube (CRT). The computer system 1200 may include an input device 1212, such as, but not limited to, a keyboard, a cursor control device 1214, such as, but not limited to, a mouse, a disk drive unit 1216, a signal generation device 1218, such as, but not limited to, a speaker or remote control, and a network interface device 1220.

The disk drive unit 1216 may include a machine-readable medium 1222 on which is stored one or more sets of instructions 1224, such as, but not limited to, software embodying any one or more of the methodologies or functions described herein, including those methods illustrated above. The instructions 1224 may also reside, completely or at least partially, within the main memory 1204, the static memory 1206, or within the processor 1202, or a combination thereof, during execution thereof by the computer system 1200. The main memory 1204 and the processor 1202 also may constitute machine-readable media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

The present disclosure contemplates a machine-readable medium 1222 containing instructions 1224 so that a device connected to the communications network 135, another network, or a combination thereof, can send or receive voice, video or data, and communicate over the communications network 135, another network, or a combination thereof, using the instructions. The instructions 1224 may further be transmitted or received over the communications network 135, another network, or a combination thereof, via the network interface device 1220.

While the machine-readable medium 1222 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that causes the machine to perform any one or more of the methodologies of the present disclosure.

The terms "machine-readable medium," "machine-readable device," or "computer-readable device" shall accordingly be taken to include, but not be limited to: memory devices, solid-state memories such as a memory card or other package that houses one or more read-only (non-volatile) memories, random access memories, or other re-writable (volatile) memories; magneto-optical or optical medium such as a disk or tape; or other self-contained information archive or set of archives is considered a distribution medium equivalent to a tangible storage medium. The "machine-readable medium," "machine-readable device," or "computer-readable device" may be non-transitory, and, in certain embodiments, may not include a wave or signal per se. Accordingly, the disclosure is considered to include any one or more of a machine-readable medium or a distribution medium, as listed herein and including art-recognized equivalents and successor media, in which the software implementations herein are stored.

The illustrations of arrangements described herein are intended to provide a general understanding of the structure of various embodiments, and they are not intended to serve as a complete description of all the elements and features of apparatus and systems that might make use of the structures described herein. Other arrangements may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Thus, although specific arrangements have been illustrated and described herein, it should be appreciated that any arrangement calculated to achieve the same purpose may be substituted for the specific arrangement shown. This disclosure is intended to cover any and all adaptations or variations of various embodiments and arrangements of the invention. Combinations of the above arrangements, and other arrangements not specifically described herein, will be apparent to those of skill in the art upon reviewing the above description. Therefore, it is intended that the disclosure not be limited to the particular arrangement(s) disclosed as the best mode contemplated for carrying out this invention, but that the invention will include all embodiments and arrangements falling within the scope of the appended claims.

The foregoing is provided for purposes of illustrating, explaining, and describing embodiments of this invention. Modifications and adaptations to these embodiments will be apparent to those skilled in the art and may be made without departing from the scope or spirit of this invention. Upon reviewing the aforementioned embodiments, it would be evident to an artisan with ordinary skill in the art that said embodiments can be modified, reduced, or enhanced without departing from the scope and spirit of the claims described below.

The invention claimed is:

1. A method for manufacturing a surgical instrument, comprising the steps:
   receiving a selection of a value for at least one parameter of the surgical instrument in a configuration program;
   automatically generating configuration data from the selected value by utilizing the configuration program, wherein the generating is performed by utilizing instructions from a memory that are executed by a processor;
   transferring the configuration data to a 3D printer;
   printing the surgical instrument by utilizing the 3D printer; and
   wherein the surgical instrument has at least one handle and at least one working end, and wherein the at least one parameter originates from a group of parameters comprising at least a subset of the following parameters: a shape of the working end, a length of the working end, a width of the working end, a thickness of the working end, a shape of the handle, a length of the handle, a width of the handle, a thickness of the handle, or a combination thereof.

2. The method of claim 1, wherein the value of the parameter corresponding to the shape of the working end can be selected from a group of values comprising at least a subset of the following values: triangular, rectangular, round, or oval-shaped.

3. The method of claim 1, wherein the value of the parameter of the length, width, and/or thickness of the working end is selected from a group of values comprising at least one specific value, advantageously a range between two specific values from within which the value can be selected.

4. The method of claim 1, wherein the value of the parameter of the shape of the handle is selected from a group of values comprising at least a subset of the following values: flat, half shell-shaped, flat with holes, or half shell-shaped with holes.

5. The method of claim 1, wherein the value of the parameter of the length, width, and/or thickness of the handle is selected from a group of values comprising at least one specific value, advantageously a range between two specific values from within which the value can be selected.

6. The method of claim 1, wherein the surgical instrument additionally has at least one shaft, and the group of parameters additionally comprises at least the following parameters: a shape of the shaft, a length of the shaft, a width of the shaft, a thickness of the shaft, or a combination thereof.

7. The method of claim 6, wherein the value of the parameter of the shape of the shaft is selected from a group of values comprising at least a subset of the following values: straight, curved, angled, or doubly angled.

8. The method of claim 6, wherein the value of the parameter of the length, width, and/or thickness of the shaft is selected from a group of values comprising at least one specific value, advantageously a range between two specific values from within which the value can be selected, preferably set in an infinitely variable manner.

9. The method of claim 1, wherein the surgical instrument is printed in an electrically conductive material by utilizing the 3D printer.

10. The method of claim 1, wherein the method further comprises the following step:

receiving selection of a material and/or a color for an insulating coating for portions of the surgical instrument.

11. The method of claim 10, wherein the method further comprises the following step:
applying the insulating coating to the surgical instrument, by utilizing the 3D printer or by spraying.

12. The method of claim 1, wherein the surgical instrument is a monopolar or a bipolar coagulation forceps.

13. The method of claim 1, wherein, in another step, receiving a selection of a type of electrical connection in the configuration program, wherein the type of electrical connection comprises a first connector for a flat cable or a second connector for a two-pin plug.

14. The method according to claim 1, wherein the surgical instrument is a hook or a retractor.

15. The method of claim 1, wherein the configuration program uses the configuration data to generate a graphic representation of the surgical instrument corresponding to the configuration data and displays the graphic representation of the surgical instrument on a graphical user interface.

16. A system for manufacturing a surgical instrument, comprising:
a memory that stores instructions;
a processor that executes the instructions to perform operations, the operations comprising:
receiving a selection of a value for at least one parameter of the surgical instrument in a configuration program;
automatically generating configuration data from the selected value by utilizing the configuration program, wherein the generating is performed by utilizing instructions from a memory that are executed by a processor;
transferring the configuration data to a 3D printer;
printing the surgical instrument by utilizing the 3D printer;
wherein the surgical instrument comprises a monopolar or a bipolar coagulation forceps or hook or retractor.

17. The system of claim 16, wherein the operations further comprise:
receiving selection of a material and/or a color for an insulating coating for portions of the surgical instrument; and
printing the surgical instrument with an electrically conductive material by utilizing the 3D printer.

18. The system of claim 16, wherein the operations further comprise utilizing the configuration data to generate a graphic representation of the surgical instrument corresponding to the configuration data and displaying the graphic representation of the surgical instrument on a graphical user interface.

19. A non-transitory computer-readable medium comprising instructions, which, when loaded and executed by a processor, cause the processor to perform operations, the operations comprising:
receiving a selection of a value for at least one parameter of a surgical instrument in a configuration program;
automatically generating configuration data from the selected value by utilizing the configuration program, wherein the generating is performed by utilizing instructions from a memory that are executed by a processor;
transferring the configuration data to a 3D printer;
printing the surgical instrument by utilizing the 3D printer; and
wherein the surgical instrument has at least one handle and at least one working end, and wherein the at least one parameter originates from a group of parameters comprising at least a subset of the following parameters: a shape of the working end, a length of the working end, a width of the working end, a thickness of the working end, a shape of the handle, a length of the handle, a width of the handle, a thickness of the handle, or a combination thereof.

20. A method for manufacturing a surgical instrument, comprising the steps:
receiving a selection of a value for at least one parameter of the surgical instrument in a configuration program;
automatically generating configuration data from the selected value by utilizing the configuration program, wherein the generating is performed by utilizing instructions from a memory that are executed by a processor;
transferring the configuration data to a 3D printer;
printing the surgical instrument by utilizing the 3D printer; and
wherein the surgical instrument is printed in an electrically conductive material by utilizing the 3D printer.

21. The method of claim 20, wherein the surgical instrument has at least one handle and at least one working end, and wherein the at least one parameter originates from a group of parameters comprising at least a subset of the following parameters: a shape of the working end, a length of the working end, a width of the working end, a thickness of the working end, a shape of the handle, a length of the handle, a width of the handle, a thickness of the handle, or a combination thereof.

22. A method for manufacturing a surgical instrument, comprising the steps:
receiving a selection of a value for at least one parameter of the surgical instrument in a configuration program;
automatically generating configuration data from the selected value by utilizing the configuration program, wherein the generating is performed by utilizing instructions from a memory that are executed by a processor;
transferring the configuration data to a 3D printer;
printing the surgical instrument by utilizing the 3D printer; and
receiving a selection of a material and/or a color for an insulating coating for portions of the surgical instrument.

23. A method for manufacturing a surgical instrument, comprising the steps:
receiving a selection of a value for at least one parameter of the surgical instrument in a configuration program;
automatically generating configuration data from the selected value by utilizing the configuration program, wherein the generating is performed by utilizing instructions from a memory that are executed by a processor;
transferring the configuration data to a 3D printer;
printing the surgical instrument by utilizing the 3D printer; and
wherein the surgical instrument is a monopolar or a bipolar coagulation forceps.

24. A method for manufacturing a surgical instrument, comprising the steps:
receiving a selection of a value for at least one parameter of the surgical instrument in a configuration program;
automatically generating configuration data from the selected value by utilizing the configuration program, wherein the generating is performed by utilizing instructions from a memory that are executed by a processor;

transferring the configuration data to a 3D printer;

printing the surgical instrument by utilizing the 3D printer; and receiving a selection of a type of electrical connection in the configuration program, wherein the type of electrical connection comprises a first connector for a flat cable or a second connector for a two-pin plug.

25. A method for manufacturing a surgical instrument, comprising the steps:

receiving a selection of a value for at least one parameter of the surgical instrument in a configuration program;

automatically generating configuration data from the selected value by utilizing the configuration program, wherein the generating is performed by utilizing instructions from a memory that are executed by a processor;

transferring the configuration data to a 3D printer;

printing the surgical instrument by utilizing the 3D printer; and wherein the surgical instrument is a hook or a retractor.

* * * * *